US00PP31215P2

(12) United States Plant Patent
Malaguerra et al.

(10) Patent No.: US PP31,215 P2
(45) Date of Patent: Dec. 10, 2019

(54) ***HOSTA* PLANT NAMED 'WU HOO'**

(50) Latin Name: ***Hosta* hybrid**
Varietal Denomination: Wu Hoo

(71) Applicants: Mark Lee Malaguerra, Atlanta, GA (US); Scott Christopher Smith, Atlanta, GA (US)

(72) Inventors: Mark Lee Malaguerra, Atlanta, GA (US); Scott Christopher Smith, Atlanta, GA (US)

( * ) Notice: Subject to any disclaimer, the term of this patent is extended or adjusted under 35 U.S.C. 154(b) by 0 days.

(21) Appl. No.: 15/969,609

(22) Filed: May 2, 2018

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353

CPC ..... A01H 5/12; A01H 5/02; A01H 5/0272; A01H 5/00; A01H 6/12; A01H 6/56
See application file for complete search history.

(56) References Cited

U.S. PATENT DOCUMENTS

PP20,774 P2 * 2/2010 Skaggs ..... A01H 5/00 Plt./353

OTHER PUBLICATIONS

The Georgia *Hosta* Society. Georgia *Hosta* Notes, vol. 33, No. 4, 2017, retrieved on Apr. 8, 2019, retrieved from the Internet at https://gahosta.org/resources/Documents/October%20Newsletter%20Final%20Copy.pdf, pp. 1 and 7. (Year: 2017).*

* cited by examiner

*Primary Examiner* — June Hwu

(57) ABSTRACT

A new and distinct cultivar of *Hosta* named 'Wu Hoo', characterized by its very large sized mounding clump, blue-green leaves with medium green margins. In combination these traits set 'Wu Hoo' apart from all other existing varieties of *Hosta* known to the inventor.

5 Drawing Sheets

Figure 1:
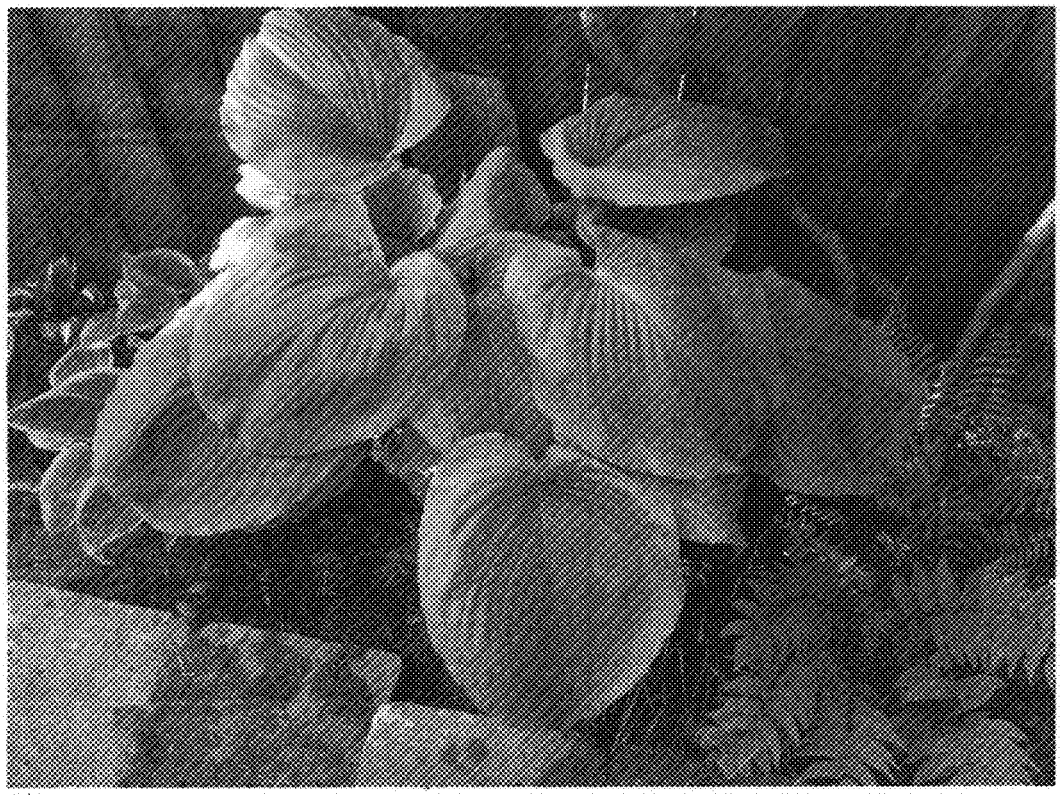

Latin name: *Hosta* hybrid.
Variety denomination: 'Wu Hoo'.

BACKGROUND OF THE INVENTION

The present invention relates to a new and distinct cultivar of *Hosta* plant, botanically known as *Hosta*, hereinafter referred to by the cultivar name 'Wu Hoo'.

The new plant was identified as a unique cultivar by the Inventor in Atlanta, USA as an offshoot of the parent plant *Hosta* 'Empress Wu'. The offshoot exhibited different physical characteristics from the parent plant (*Hosta* 'Empress Wu') approximately 12 months after said parent plant was initially planted and grown in a pot in the Atlanta, Ga. garden of Mark Malaguerra and Scott Smith. Upon identification of the variation from the main plant, the new plant that exhibited unique characteristics was separated from the main plant and grown separately to verify that it would continue to exhibit the unique characteristics over time.

The parent plant, 'Empress Wu' is a U.S. Plant Pat. No. 20,774 and has been well documented as to its primary characteristics. The hybrid of 'Empress Wu' that is the subject of this patent application exhibits significantly different characteristics from the parent so as to warrant recognition as an entirely separate hybrid. This hybrid has been recognized and registered by the American *Hosta* Society as *Hosta* 'Wu Hoo'.

As of the initial filing, there was one (1) other registered hybrid of 'Empress Wu', *Hosta* 'Wu La La' (PPAF). 'Wu Hoo' differs from 'Wu La La' in that the leaves of 'Wu Hoo' are more rounded than 'Wu La La' which has heart shaped leaves. The margin variegation of 'Wu Hoo' are significantly wider than that which is exhibited by 'Wu La La'. In addition, the leaves of 'Wu La La' exhibit a wavy texture in the centermost portions of the leaves in a similar manner to 'Empress Wu' whereas 'Wu Hoo' does not exhibit the wavy texture in the leaf centers.

The new plant differs from its parent primarily in that the margin areas of the leaves produce anthocyanins that produce a blue-green variegation where the parent plant was solid green on the upper surface of the leaf. The new plant also exhibits leaves which are more rounded with slight convex curvature which is significantly different from the parent plant which displays a slight concave, to almost flat curvature to the leaves and a moderate corrugation or waviness to the leaf structure.

The flower scapes and flowers of both the parent plant and the hybrid 'Wu Hoo' appear identical both in terms of size and color but also in terms of time of year both plants flower in the Atlanta, Ga. garden in which they are planted.

Asexual propagation of the new cultivar by division in 2014 in Atlanta, Ga. USA and by meristem tissue culture in 2015 in Olathe, Kans. USA has shown the unique and distinct characteristics of this new plant are stable and reproduce true to type in successive generations. These asexually propagated plants are currently being grown in a greenhouse by Green Hill Farm. The first asexually reproduced plants which were propagated by meristem tissue culture in 2015 are currently growing in the Atlanta, Ga. and Waynesville, N.C. gardens of Mark Malaguerra and Scott Smith and exhibit the same physical characteristics as the originally identified hybrid.

SUMMARY OF THE INVENTION

The following traits have been repeatedly observed and are determined to be the unique characteristics of 'Wu Hoo'.

These characteristics in combination distinguish the new *Hosta* as a new and unique cultivar:

1. Very large sized mounding clump;
2. Leaves emerge with blue-green centers and irregular light-green margins, the margins are at least ½ inch in width;
3. Leaves age to a blue-green center with irregular medium green margin;
4. Leaves are very large, rounded and corrugated;
5. Leaves are slightly convex;
6. Light lavender flowers on green scapes.

The new *Hosta* can be compared to the cultivar, *Hosta* 'Empress Wu' (patented). In the new *Hosta*, the leaves are variegated with a light to medium-green margin on blue-green leaves as compared to the leaves of *Hosta* 'Empress Wu' which are solid blue-green. The leaves of the new *Hosta* are more rounded and have a heavier substance than 'Empress Wu'. Where the leaves of 'Empress Wu' have a slight curve upwards, the substance of 'Wu Hoo' differs in that it is less rigid to the extent that the leaves have a slight downward curve.

Other aspects of the new *Hosta* such as scapes, flowers and seeds are consistent with the description of *Hosta* 'Empress Wu."

The new *Hosta* cultivar has not been observed under all possible environmental conditions. The phenotype may vary to some extent with variations in environmental conditions such as temperature, fertility and light intensity, but without any variance in the genotype.

BRIEF DESCRIPTION OF THE PHOTOGRAPHS

The accompanying color photographs illustrate the overall appearance of the new cultivar including its unique traits as a 4 year old plant growing in a 4 gallon container. The colors are as true as is reasonably possible with conventional photography.

FIG. 1 was taken in May of 2014 and comprises a top perspective of the entire plant.

Figure 2:
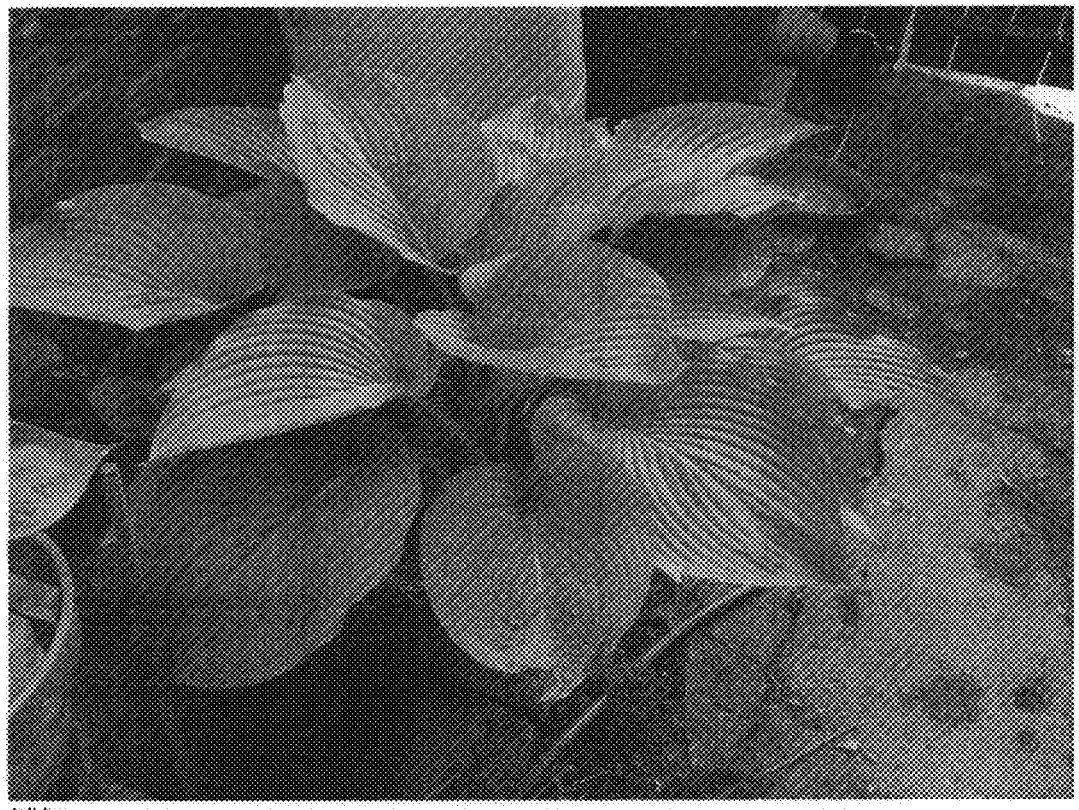

FIG. 2 was taken May of 2014 and shows parent plant 'Empress Wu' from which the hybrid was taken.

Figure 3:
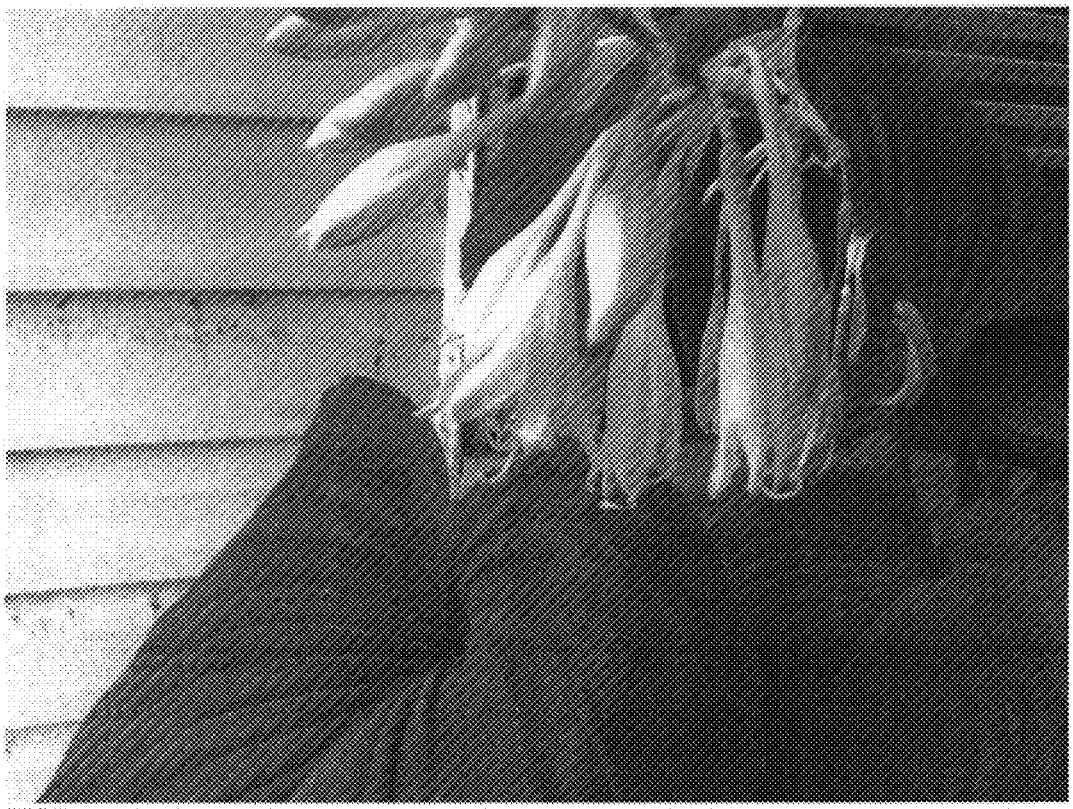

FIG. 3 was taken in May of 2017 and shows a close up of the flower scape.

Figure 4:
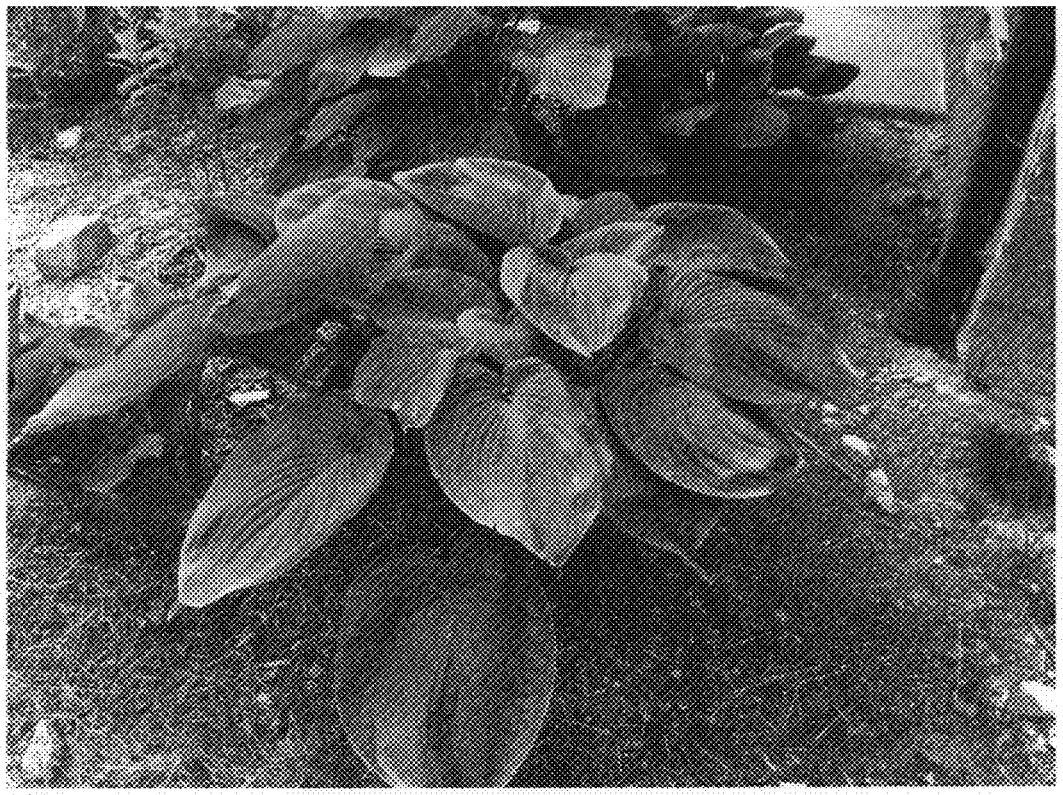

FIG. 4 shows the entire clump of 'Wu Hoo' in the ground (parent plant in background) and was taken in June of 2017.

Figure 5:
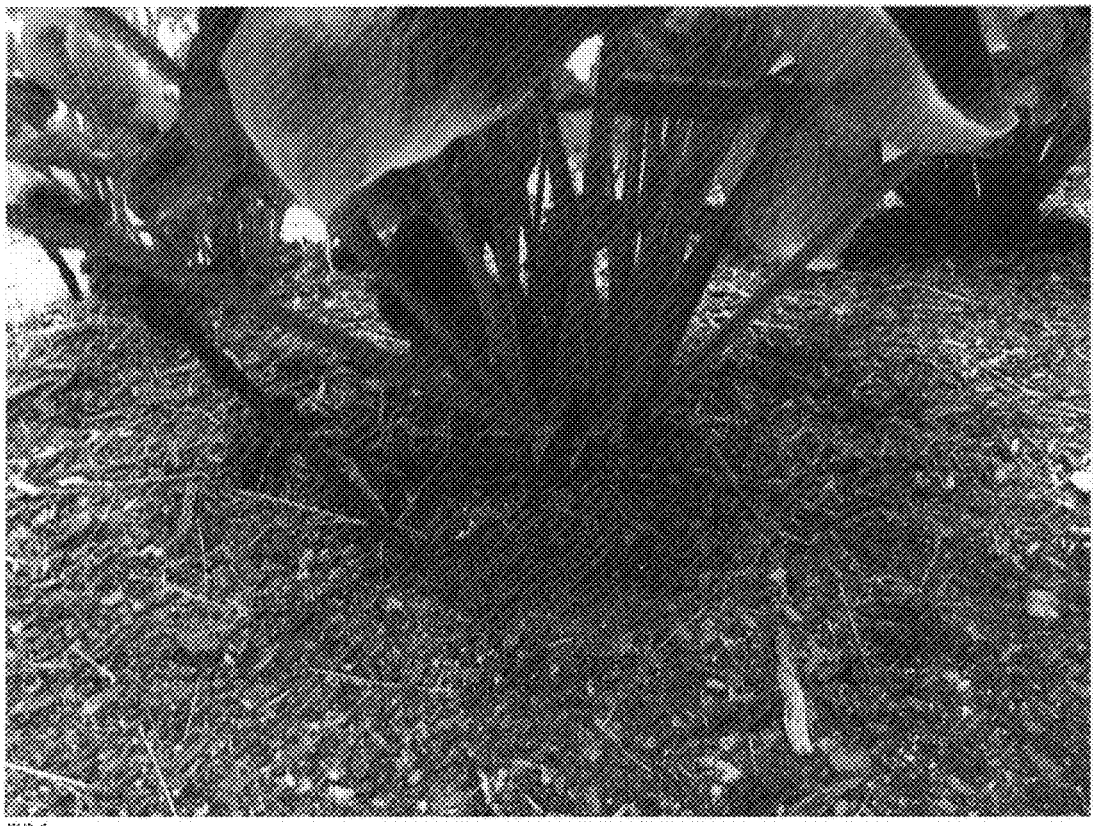

FIG. 5 was taken in June of 2017 and shows the base of the plant.

DETAILED DESCRIPTION OF THE INVENTION

In the following description, color references are made to The Royal Horticultural Society's Colour Chart (2001 edition) except where general terms of ordinary dictionary significance are used. The following observations and measurements describe a 4-year old plant growing in a four (4) gallon container, as depicted in the accompanying photographs, which was grown outdoors in in the Atlanta, Ga., USA garden of Mark Malaguerra and Scott Smith.

Botanical classification: *Hosta* 'Wu Hoo'.

Parentage: *Hosta* 'Empress Wu' (patented).

Propagation:

*Method*.—By division and meristem tissue culture.

Plant description:

*Plant habit*.—Very large, mounding, symmetrical.

*Culture*.—Light to medium shade in moist, well-drained soil.

*Plant type*.—Herbaceous rhizomatous perennial.

*Plant height*.—24 inches.

*Plant width*.—At least 46 inches.

*Growth rate*.—Vigorous.

*Root system*.—Normal, fleshy, branching from central rhizome.

*Disease resistance*.—No known resistance or susceptibility to disease known to *Hosta* has been observed.

*Plant hardiness zone*.—3-9.

*Foliage description*.—Leaf shape — Nearly Round, broadly cordate with apiculate leaf apex. Slight twisting at apex present in most leaves. Leaf blistering is absent under typical growing conditions. For *Hosta*, typical growing conditions are protection from direct sun during summer months in Atlanta, Ga. Leaf margin — slightly rippled. Leaf surface — Dull blue with 2-inch, light green margins. Leaf texture — Moderate substance, veins impressed, leaves cup downward on mature leaves. Leaf dimensions — 17 inches in width, 17 inches in length. Venation pattern — Campylodrome with 15 to 16 pairs of veins, the same blue-green color as the leaves (about RHS 133C). Leaf color — The leaves in spring are blue-green (about RHS 133C) with a 2-inch light green margin (about RHS 134C). The back of the leaves is a dull green (about RHS 138C). The leaves become dark green and slightly glaucous (about RHS 133A) with green margins becoming slightly more dark (about RHS 134B) later in the season during the blooming.

Petiole description: Plant petioles have a length of approximately 19 to 20 inches with a diameter of about 0.78 inches wide. The petiole color is moderate green (RHS 142B).

Flower description:

*Bloom period*.—Late Spring (late May — mid June in Atlanta, Ga. which is a climate zone of 7b to 8).

*Fragrance*.—None.

*Flower arrangement*.—Raceme of numerous single horizontal to drooping flowers comprised of six tepals. The number of flowers per raceme varies from about 30 to 40 with each flower lasting approximately one day over a period of about 4 weeks.

*Flower shape*.—Clavate with bluntly acute apex and longer thin base.

*Perianth*.—Funnel in shape.

*Flower dimensions*.—Approximately 1.5 inches wide and 2.5 inches long.

*Flower color*.—Light lavender (about RHS 91B).

*Bud color*.—Light lavender (about RHS 92D).

*Bud dimensions*.—2¼ inches in length and ½ inches in width.

*Tepal color*.—Inner tepal color is about RHS 91D on the outside and shades to about RHS 76C on the inside.

*Tepal apex shape*.—Acute.

*Tepal dimensions*.—Approximately 2.5 inches long and 1.5 inches wide.

*Bract color*.—Lowest bracts approximately RHS 138B on top and bottom surfaces and approximately RHS 138D on the basal top portion.

*Bract length*.—Lowest are up to 3.25 inches long and 0.6 inches wide, growing progressively smaller in both length and width.

*Peduncle*.—One per mature division. Average length is forty-two (42) inches tall at full maturity×¼ inch diameter at base. Emerges above the leaf scope upright, becoming moderately arching as it matures. Peduncle color is RHS 138D.

*Pedicel*.—⅞ inches in length×1/16 inch in diameter. Color is closest to RHS 138D.

*Corolla*.—Average length of the corolla tube is 2¼ inches. The outer lobes of the corolla average ¼ in length. The inner corolla has an average length of 1 inch.

*Pollen*.—Color is close to RHS 14A.

Scape description:

*Number*.—The number of scapes per plant is dependent on the maturity of the plant. Each mature eye comprising the clump may produce a single flower scape under normal growing conditions.

Description of reproductive organs: The reproductive organs are typical of the genus *Hosta* and comprise six stamens and a compound ovary having three locules. The stamen color is yellowish white (about RHS 155B); the anther color is moderate red (about RHS 183C); the pistil color is yellowish white (about RHS 155B); and the stigma color is yellowish white (about RHS 155B). The stamen length is about 2½ inches and the pistil length is about 2¾ inches, curved 180 degrees at the end.

Fruit: Tri-dehiscent capsule about 1⅛ inches long and 3/16 inches in diameter; variable in color strong yellowish green (about RHS143C) with more red or more green.

Seed development: Single winged drupe about ½ inches long and ⅛ inches wide, number per pod variable about 5 to 10, color dark gray purple (about RHS 202A).

Root development: From transfer to rooting media in tissue culture, rooting takes approximately 4 weeks at about 68 degrees Fahrenheit. After transfer from stage III in tissue culture to planting into soil in a greenhouse, a well rooted plant is produced in approximately 8 weeks with a daytime temperature of about 68 degrees Fahrenheit and a soil temperature of about 78 degrees Fahrenheit.

We claim:

1. A new and distinct cultivar of *Hosta* plant named 'Wu Hoo' as illustrated and described herein.

* * * * *